United States Patent [19]

Laughlin et al.

[11] 4,263,281

[45] Apr. 21, 1981

[54] OXAALKANOATE ANTI-ULCER COMPOSITION

[75] Inventors: Robert G. Laughlin; Juian-Juian L. Fu, both of Cincinnati, Ohio

[73] Assignee: The Procter & Gamble Company, Cincinnati, Ohio

[21] Appl. No.: 57,922

[22] Filed: Jul. 16, 1979

[51] Int. Cl.³ ...................... A61K 33/00; A61K 33/12; A61K 33/08; A61K 31/205
[52] U.S. Cl. .................................... 424/155; 424/127; 424/156; 424/157; 424/316
[58] Field of Search ............... 424/157, 156, 155, 127, 424/316

[56] References Cited

U.S. PATENT DOCUMENTS 3,822,344    7/1974    Corker .................................. 424/316

*Primary Examiner*—Frederick E. Waddell
*Attorney, Agent, or Firm*—Jerry J. Yetter; Steven J. Goldstein; Richard C. Witte

[57] ABSTRACT

Certain oxaalkanoate zwitterionic surfactant-type compounds and their esters provide oral therapy for ulceration of the gastric mucosa. The oxaalkanoate zwitterionic compounds are especially preferred compositions used in the management of both gastric and duodenal ulcers.

11 Claims, No Drawings

OXAALKANOATE ANTI-ULCER COMPOSITION

TECHNICAL FIELD

The present invention relates to compositions and processes for preventing or relieving ulceration of the gastric mucosa. More specifically, certain oxaalkanoate zwitterionic surfactant-type compounds have now been found to be effective in the management of so-called "peptic" ulcers. The oxaalkanoate zwitterionics disclosed herein can be administered alone to treat ulcers, and can be used in conjunction with conventional antacids to reduce or prevent the stomach irritation, pain and "gas" often associated with ulcers.

Ulceration of any portion of the gastric mucosa is commonly referred to by the lay person as "an ulcer". Medically, ulcers are more precisely defined by their situs in the gastrointestinal tract. Thus, duodenal ulcers most commonly occur in the duodenal bulb. Gastric ulcers most commonly occur along the lesser curvature of the stomach. Ulcers can also form in the pyloric canal, in a position in the duodenum beyond the duodenal bulb, in the jejunum, etc. Such ulcers are referred to as channel ulcers, postbulbar ulcers, marginal or stomal ulcers, and jejunal ulcers. Etiologically, ulceration appears to be caused by a lack of balance between the ulcer-promoting factors, such as stomach acid and pepsin, and the mucosal protective factors, such as the production of gastric mucus, membrane barriers to permeability, or mucosal cell turnover time.

Single or multiple gastric or duodenal ulcers are often directly related to stress, including psychological stress and stress related to trauma such as burns, surgery, shock, excessive salicylate therapy, and the like.

By the present invention, oxaalkanoate compounds are administered orally to decrease or prevent ulceration of the gastrointestinal tract.

BACKGROUND ART

Long-chain materials have been suggested for use in the treatment of gastric and duodenal ulcers: J5-2025-706 and J5 2025-711. These two Japanese patents relate, respectively, to polyunsaturated long-chain alcohols and polyunsaturated esters of long-chain alcohols used for this purpose.

Lore and Luciano, *Physiology and Behavior* 18, 743–45 (1977) have observed that stress phenomena cause ulcers in rats in a laboratory test situation and propose physiologic mechanisms to explain this observation.

U.S. Pat. No. 3,922,341 teaches means for increasing blood oxygen levels (previously decreased by lung disease) by administering a carboxy zwitterionic compound.

The co-pending application of Brown and Laughlin, Ser. No. 057,923, filed July 16, 1979, discloses the synthesis of oxaalkanoate zwitterionic surfactants of the type disclosed herein.

DISCLOSURE OF INVENTION

The present invention encompasses compositions and means for treating and/or preventing ulcers in humans and lower animals. Oxaalkanoate compounds are provided in convenient unit dosage form for oral administration to the ulcer patient.

The oxaalkanoate zwitterionic compounds employed in the practice of this invention are of the general formula

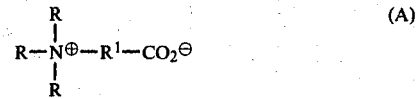

wherein at least one R group is a lipophilic substituent; and $R^1$ is an oxygen-interrupted hydrocarbylene substituent, said substituent $R^1$ preferably having a chain length no greater than about 11 total atoms.

Ester salts of the formula (A) zwitterionics which hydrolyze under physiologic conditions to provide the zwitterionic in situ also encompassed by this invention. Such compounds are of the formula

wherein $R^2$ is a hydrocarbyl substituent, e.g., methyl, ethyl, propyl, etc., and X is a halogen ion, especially bromide. Such esters are included in the term "oxaalkanoate zwitterionic surfactant compound" as used herein.

The syntheses of various oxaalkanoate zwitterionic surfactant compounds are described in detail, hereinafter.

As pointed out in the copending application of Brown and Laughlin, cited above, various oxaalkanoate zwitterionic compounds wherein at least one lipophilic R group contains greater than about 10 or 12 carbon atoms are readily prepared and are excellent detergents. However, the compounds wherein R is $C_{14}$ through about $C_{22}$ and wherein $R^1$ is, especially, —$CH_2CH_2OCH_2CH_2OCH_2CH_2OCH_2$—, are especially effective anti-ulcer agents.

Preferred oxaalkanoate zwitterionic anti-ulcer compounds used herein are of the formula

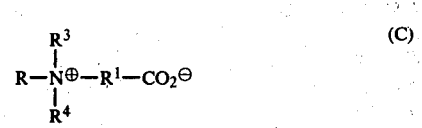

or cationic ester salts thereof, per formula (B).

The formula (C) compounds are characterized by: R as a hydrocarbyl moiety greater than $C_{10}$, including $C_{11}$ and higher alkyl (preferred), alkenyl, alkynyl, alkaryl and arylalkyl substituents; $R^3$ and $R^4$ which may be the same (preferred) or different hydrocarbyl moieties in the manner of R, but preferably $C_{10}$, or smaller; and $R^1$ is an alkylene oxide moeity with a chain length no greater than about 11 total atoms, preferably ethylene oxide of the formula —$(CH_2CH_2O)_nCH_2CH_2$—, —$(CH_2CH_2O)_nCH_2$— or propylene oxide

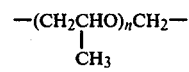

wherein the integer n is 1, 2 or 3, or higher, with n as 3 being the highly preferred.

The most highly preferred, oxaalkanoate anti-ulcer compounds are those of formula (C) (or the B ester form) wherein R is $C_{14}$ to about $C_{22}$ alkyl, $R^3$ and $R^4$ are each short chain alkyl, e.g., methyl, ethyl and propyl, and $R^1$ is, —$CH_2CH_2$—O—$CH_2$—$CH_2$—O —$CH_2CH_2$—O—$CH_2$—, i.e., the "ammonio trioxaundecanoates".

The foregoing oxaalkanoate compounds herein can also have two of the shorter chain R groups (e.g., $R^3$ and $R^4$ in formula C) joined with one another around the nitrogen atom to provide a homocyclic or heterocyclic ring, e.g., piperidinio, morpholinio, and the like. Such compounds are also useful in the practice of the present invention.

It is to be understood that the oxaalkanoate zwitterionic compounds defined by the foregoing formulae all exhibit the desirable pharmacological activity disclosed herein. Some of the compounds are more pharmaceutically active than others and these are preferred for drug use. The N,N'-dimethylammonio trioxaundecanoate compounds ("ATOU") are readily prepared, and are preferred anti-ulcer agents.

BEST MODE

Ulcer therapy and/or prophylaxis according to the present invention comprises simply administering the oxaalkanoate compound orally to a patient in need of such treatment. Any convenient oral dosage form can be used, and single dosages can range from about 18 mg to 2500 mg, and higher. Multiple dosages can be administered daily, as needed. Optimally, the oxaalkanoate compound is administered prior to mealtimes, but food protein does not interfere with anti-ulcer activity.

Of course, the total daily usage of the compounds herein will be decided by the attending physician. For example, the usage rate for the oxaalkanoate compositions will be determined by such factors as the type of disease state being treated, the age and weight of the patient, the severity of the condition, the length of time the patient will be undergoing therapy and like factors well known in the medical arts. In general, oral treatment regimens according to the present invention comprise orally administering to a human or lower animal in need of such treatment from about 10 mg/kg to about 3000 mg/kg (preferably 25 mg/kg-500 mg/kg) per day of the oxaalkanoate compound, especially, the N,N-dimethyl-ammonio trioxaundecanoate ("ATOU") compounds whose synthesis is disclosed in detail, hereinafter. The $C_{14}$ATOU, $C_{16}$ATOU, $C_{18}$ATOU, $C_{20}$ATOU, $C_{22}$ATOU compounds, and their respective esters (the ethyl esters are convenient) are especially preferred anti-ulcer agents used herein. (By "mg/kg" herein is meant milligrams per kilogram of patient body weight; see Animal Testing, hereinafter.)

For purposes of oral administration, the compounds of this invention can be formulated as capsules, tablets, chewable tablets, powders, granules, solutions, suspensions, or the like. For treatment of non-human animals, the compounds are preferably incorporated in animal feeds, feed supplements or feed concentrates.

The oxaalkanoates are orally administered, preferably in unit dosage form in combination with excipients such as solid or liquid fillers, diluents or encapsulating substances which provide a pharmaceutical carrier, e.g., materials commonly used in the manufacture of tablets, capsules, elixirs, and the like. Some examples of the substances which can serve as pharmaceutical carriers herein include sugars such as lactose, glucose and sucrose; starches such as corn starch and potato starch; cellulose and its derivatives, such as sodium carboxymethylcellulose, ethylcellulose and cellulose acetate; powdered gums; malt; gelatin; stearic acid; calcium sulfate; vegetable oils, such as peanut oil and cottonseed oil; mineral oil; polyols such as propylene glycol, glycerin, sorbitol, mannitol and polyethylene glycol; agar; alginic acid; as well as other non-toxic, compatible substances used in pharmaceutical formulations. Wetting agents and lubricants, coloring agents, flavoring agents and preservatives can also be present. Enteric coatings can be used in standard fashion to provide prolonged release of the compositions and/or release in the intestines rather than in the stomach.

The oxaalkanoates can optionally be co-administered orally with an effective amount of an antacid. Aluminum hydroxide (hydrated alumina, available as Amphojel ®, Aldrox ®, etc.), magnesium oxide, magnesium carbonate, calcium carbonate, magnesium trisilicate, magnesium hydroxide, and mixed magnesium-/aluminum oxides and hydroxides, all of which are well-known antacids used in the management of duodenal and gastric ulcers, can be incorporated in the compositions of the present invention at their common usage levels (generally 100-500 mg antacid per unit dose, although more or less can be used, according to the desires of the formulator).

The compositions herein can be prepared by formulation and tableting techniques commonly used in the pharmaceutical industry.

The following animal tests illustrate the excellent anti-ulcer results obtained by orally administering oxaalkanoate compounds in the manner of this invention.

Animal Testing

Oxaalkanoate compounds were tested for anti-ulcer activity in the Shay Rat Pylorus-Ligation Gastric Ulcer Test. The details of the Shay Rat test system are found in general texts. The test indicates that optimal anti-ulcer activity for the oxaalkanoate is in the range of about 25-500 mg/kg/day. While higher dosages can be used, dosages of up to about 100 mg/kg four times each day (before meals and at bedtime) are conveniently administered, orally.

As can be seen from the following data, representative oxaalkanoate compounds of the present type are excellent anti-ulcer agents, both with regard to incidence and severity of ulcers.

| ANIMAL TEST DATA | |
|---|---|
| Ulcer Incidence (%) Test | |
| Treatment | 100 mg/kg |
| $H_2O$ Control (avg.) | 100% |
| $C_{14}$ATOU | 25% |
| $C_{22}$ATOU | 25% |
| $C_{14}$ATOU ethyl ester | 14% |
| Ulcer Severity Test* | |
| $H_2O$ Control | 4.8 |
| $C_{14}$ATOU | 1.8 |
| $C_{22}$ATOU | 1.2 |
| $C_{14}$ATOU ethyl ester | 1.1 |

*A reading of 1 in the severity grade indicates inflammation, but no ulceration. Grades above 1 indicate ulceration.

The following examples further illustrate the practice of this invention but are not limiting thereof.

EXAMPLE I

| Ingredient | mg. per capsule |
|---|---|
| $C_{14}$ATOU | 1000 |

Four gelatin capsules of the above type are administered orally at three hour intervals four times daily to substantially reduce duodenal ulceration in a human or animal in need of such treatment.

EXAMPLE II

Tablets are prepared by conventional methods, as follows:

| Ingredient | mg. per tablet |
|---|---|
| C22ATOU | 500 |
| Starch | 50 |
| Lactose | 50 |
| Hydrated alumina* | 100 |
| Magnesium stearate** | 1.5 |

*Conventional antacid
**Tableting aid and lubricant

Two tablets of the above type are administered orally six times daily to substantially reduce the pain associated with duodenal ulceration.

In the tablets of Example II, the hydrated alumina is replaced by an equivalent amount of magnesium oxide, magnesium carbonate, mixed magnesium/aluminum oxides and hydroxides, calcium carbonate, magnesium trisilicate, and magnesium hydroxide, respectively, and equivalent results are secured.

Industrial Applicability

The following reaction sequence is convenient and is universally applicable for preparing the oxaalkanoate zwitterionic compounds employed in the present invention.

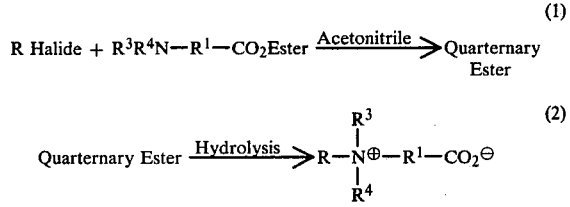

Both organo bromides and iodides can be used in Step 1. Reaction of the organo halide with the amine is carried out at reflux over a period of several hours.

The amine materials used in Step 1 can be synthesized by art-disclosed processes. In general, sodium salts of alkanol amines (amino alkoxides) can be reacted with sodium chloroacetate to provide the carboxyl terminal group. The carboxyl substituent is esterified (conveniently, methyl or ethyl ester) prior to reaction with the organo halide. Alternatively, alkanolamines are reacted with acrylonitrile and the resulting aminoalkoxypropionitriles converted to the corresponding aminoalkoxypropionate ester.

The hydrolysis of the quaternary ester (Step 2) can be performed under a variety of conditions giving rise to a wide range of yields and workup procedures. By far the most efficient method, where applicable, is that of ion-exchange chromatography. Thus, an aqueous or alcoholic solution of quaternary ester is treated on an OH$^-$ form anion exchange resin near room temperature. The exchange of halide for hydroxide and subsequent hydrolysis occur rapidly at or near room temperature. The desired zwitterionic material is obtained essentially free of inorganic halides. This method represents a considerable improvement over alcoholic hydrolysis under reflux in that fewer side reactions occur and formation (and removal) of inorganic halides is not involved in the reaction and product isolation.

The preparation of representative oxaalkanoate compounds and esters thereof of the type used in the practice of this invention is described in the following examples.

EXAMPLE III

Preparation of n—$C_{22}H_{45}N^{\oplus}(CH_3)_2CH_2CH_2OCH_2CH_2CO_2^{\ominus}$ 3-(Dimethylaminoethoxy)-propionitrile prepared in the manner disclosed in Bull. Soc. Chim. Fr. 1960, 1162 (42.0 g) was hydrolyzed in the presence of p-toluenesulfonic acid monohydrate (133.2 g) and absolute ethanol (16.1 g) for 15 hours at about 80° C. to produce, after distillation, the clear liquid ethyl 6-(dimethylamino)-4-oxahexanoate ester.

Commercial docosylbromide (3.90 g) and the foregoing oxahexanoate ester (1.90 g) were heated to reflux in acetonitrile (8 hours) to yield an off-white solid upon cooling and ether trituration. The isolated solid product was recrystallized from acetone to produce the quaternary ester, ethyl 6-docosyldimethylammonio-4-oxahexanoate bromide.

The foregoing quaternary ester bromide (24.0 g) was diluted in a 50:50 methanol:$H_2O$ (75 ml) mixture and treated with sodium carbonate $Na_2CO_3$ (8.90 g) at 60° C. (3 hours). The reaction mixture was cooled (0° C.) and the inorganic ppt filtered. The resulting supernatant was passed through a mixed-bed resin (70 g; Rexyn 300 (H-OH)) and dried to produce an off-white solid. This material was crystallized from $CHCl_3$/acetone to yield the title compound.

In like fashion are prepared the $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{23}$, $C_{24}$, $C_{25}$, $C_{26}$, $C_{27}$, $C_{28}$, $C_{29}$ and $C_{30}$ 6-dimethylammonio-4-oxahexanoate compounds from the respective n-alkyl bromides.

EXAMPLE IV

PREPARATION OF n—$C_{14}H_{29}N^{\oplus}(CH_3)_2(CH_2CH_2O)_3CH_2CO_2^{\ominus}$ Commercial $Cl(CH_2CH_2O)_3H$ (abb. $ClE_3H$) (2.0 mole) and dimethylamine (20.0 mole) were mixed in a flask (3.0 l) fitted with a condenser and stirred (RT) for 30 hours. TLC (Si-gel) examination showed the complete consumption of the $ClE_3H$. Excess dimethylamine was removed by two consecutive evaporations under reduced pressure. The residual material was reconstituted in $CHCl_3$, dried ($MgSO_4$), filtered and evaporated to dryness to produce the product, 8-dimethylamino-3,6-dioxaoctanol.

A warmed (50° C.) solution of 8-dimethylamino-3,6-dioxaoctanol (83.0 g) and NaH (26.9 g) in tetrahydrofuran under argon was treated with sodium chloroacetate (58.5 g), by dropwise addition, and refluxed (12 hours). The cooled reaction mixture (RT) was diluted with acidic ethanol ($H_2SO_4$—10%; 2.0 l), evaporated to dryness, reconstituted with ethanol and refluxed (8 hours). The hot solution was then evaporated to a viscous oil and poured onto salt (NaCl 80 g) ice (400 g) and neutralized with concentrated aqueous ammonia (pH 9.0). The final basic solution was extracted with chloroform (3×30 ml) and dried ($MgSO_4$). The solution was filtered and evaporated to dryness to produce 72.0 g of ester. This liquid was distilled to yield ethyl 11-dimethylamino-3,6,9-trioxaundecanoate as a clear liquid.

Tetradecylbromide (17.5 g) and ethyl 11-dimethylamino-3,6,9-trioxaundecanoate ester (15.0 g) were heated (95° C.) overnight. The reaction mixture was titurated with ether and evaporated to dryness under vacuum (F1.0 mm Hg) for 12 hours.

The preceding quaternary ester bromide in ethanol (90%) was eluted successively through a base-resin Rexyn 201 (HO$^-$)) and mixed-bed resin (5.0 g; Rexyn 300 (HO$^\ominus$,H$^\oplus$)). Each column was eluted with a second volume of ethanol to dislodge any weakly-bound product. The solution was filtered to remove extraneous resin; and evaporated to dryness. The title compound was isolated as a viscous liquid.

In like manner are prepared the following alkyl dimethyltrioxaundecanoate zwitterionic compounds from the respective alkyl halides and ethyl 11-dimethylamino-3,6,9-trioxaundecanoate ester: the n—$C_{16}H_{33}$ compound; the n-$C_{18}H_{37}$ compound; the n—$C_{20}H_{41}$ compound; the n—$C_{22}H_{45}$ compound. The above-described synthesis scheme appears to be appropriate for the manufacture of any of the alkyl N,N-dimethylammoniotrioxaundecanoate compounds disclosed herein. Accordingly, in like fashion are prepared the corresponding $C_{10}$, $C_{11}$, $C_{12}$, $C_{13}$, $C_{15}$, $C_{17}$, $C_{19}$, $C_{21}$, $C_{23}$, $C_{24}$, $C_{25}$, $C_{26}$, $C_{27}$, $C_{28}$, $C_{29}$ and $C_{30}$ n-alkyl N,N-dimethylammoniotrioxaundecanoate compounds and their esters.

EXAMPLE V

Preparation of

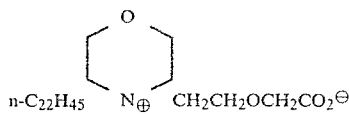

Commercial N-2-hydroxyethylmorpholine (26.40 g), and sodium chloroacetate (34.0 g) were heated (60° C.) under reduced pressure (5.0 mm), treated with 50% NaOH (25.30 g) by dropwise addition and permitted to stand overnight. The reaction mixture was cooled to room temperature and the viscous white residue was diluted with acidic ethanol (H$_2$SO$_4$—ethanol; 25:100). A white residue was removed by filtration and the solution refluxed (10 hours). The volatile solvents were removed under reduced pressure to produce a viscous solution which was poured onto salted ice (NaCl—400 g), neutralized in NH$_4$OH to pH 9.0 and extracted with CHCl$_3$. The CHCl$_3$ solution was dried (MgSO$_4$), the solvent evaporated, and the residue distilled to yield ethyl 5-(N-morpholino)-3-oxapentanoate.

Docosyliodide (14.50 g) and ethyl 5-(N-morpholino)-3-oxapentanoate (14.50 g) were heated (165° C.) overnight to form at room temperature a brown solid which was recrystallized from acetone to yield the docosyl morpholinio quaternary ester iodide. The isolated quaternary (28 g) was dissolved in 200 ml ethanol, diluted with K$_2$CO$_3$.1½ H$_2$O (14.20 g) and heated (80° C.) for 4 hours. The reaction mixture was cooled to RT, filtered, and eluted through mixed bed resin (100 g; Rexyn 300 (H—OH)) to remove ionic impurities. Evaporation of the alcohol solution produced the title compound.

EXAMPLE VI

Preparation of

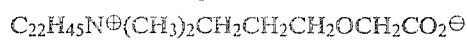

Ethyl-6(dimethylamino)3-oxahexanoate ester. Under argon, 3-dimethylaminopropanol (103.20 g) was added dropwise to NaH (28,80 g) in dry tetrahydrofuran (THF) (0.30 l) and refluxed (4 hours). A slurry of dry sodium chloroacetate (163.10 g) in THF (0.20 l) was added carefully to the preceding mixture (RT) and refluxed (24 hours). The resulting white resinous residue was neutralized with acidic ethanol (0.40 l; 5% vol. H$_2$SO$_4$), evaporated to dryness under reduced pressure to remove traces of THF, further diluted with acidic ethanol (0.50 l; 10% vol. H$_2$SO$_4$) and refluxed (8 hours). The cooled reaction mixture (RT) was filtered to remove white precipitate, evaporated to dryness, poured onto salted (NaCl: 100 g) ice and neutralized with NH$_4$OH (pH 9.0). The solution was extracted with CHCl$_3$ (3×0.30 l) and dried (MgSO$_4$). Subsequent filtration and solvent evaporation produced the desired product as a liquid (137.0 g; 65.0%); bp=88°/2.70 mm.

Ethyl-6(dimethylamino)3-oxahexanoate ester (10.61 g; 0.050 mole) and docosylbromide (18.30 g) were diluted with acetonitrile (0.025 l) and heated (95° C.) for 24 hours. The cooled reaction mixture produced a solid which crystallized from acetone to yield (23.90 g; 85%) as white crystals of ethyl 6(dimethyldocosylammonio)3-oxahexanoate bromide. The product was examined by TLC (Silica Gel; CHCl$_3$/MeOH/H$_2$O 80:25:3.0) and found to exhibit a single spot.

Ethyl 6(dimethyldocosylammonio)-oxahexanoate bromide (12.0 g; 0.020 mole) was dissolved in ethanol (0.04 l; 90%) and eluted through two successive ion-exchange resin columns which contained base resin (72.0 g wet; Rexyn 201-HO) and mixed-bed resin (15.0 g wet; Rexyn 300—H—OH). The column eluant was evaporated to dryness and the residue crystallized from CHCl$_3$-hexane to produce white crystals (9.0 g) of the title compound.

In like fashion are prepared the $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{23}$, $C_{24}$, $C_{25}$, $C_{26}$, $C_{27}$, $C_{28}$, $C_{29}$ and $C_{30}$ 6-dimethylammonio-3-oxahexanoate compounds from the corresponding n-alkyl bromides.

EXAMPLE VII

Standard pharmaceutical gelatin capsules containing 50 mg. of the compounds of any of Examples III through VI herein, respectively, are prepared using conventional methods.

One 500 mg. gelatin capsule of any of the foregoing is administered orally four times daily at regular intervals (preferably before mealtimes and at bedtime) to reduce the incidence of ulceration of the gastrointestinal muscosal lining.

EXAMPLE VIII

In a modification of the capsules of Example VII, the Example III through VI compounds are replaced by 500 mg. of their respective ethyl esters and equivalent results are secured.

EXAMPLE IX

Chewable tablets are prepared in the manner of Example II comprising 250 mg. of magnesium-aluminum hydroxide (hydrated magnesium aluminum oxide) and 250 mg. of any of the compounds of Examples III through VI herein, or their $C_1$–$C_5$ esters. Two tablets are chewed and swallowed three times daily to reduce excess stomach acidity and to reduce stomach ulceration.

As can be seen from the foregoing, the present invention provides a variety of convenient unit dosage forms of the anti-ulcer agents herein which comprise safe and effective amounts of the oxaalkanoate zwitterionic compounds, or their esters, the balance of said compositions comprising a pharmaceutically-acceptable carrier.

What is claimed is:

1. A composition of matter for treating or preventing ulcers in humans or lower animals in unit dosage form for oral administration, comprising: (a) a safe and effective amount of a zwitterionic compound of the formula

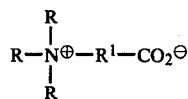

wherein: at least one R group is a lipophilic hydrocarbyl substituent containing greater than about 10 carbon atoms, and the remaining R groups are hydrocarbyl moieties containing 10 or fewer carbon atoms; and $R^1$ is an alkylene oxide moiety with a chain length no greater than about 11 total atoms, or an ester salt thereof; and (b) the balance of the composition comprising a pharmaceutically-acceptable carrier.

2. A composition according to claim 1 which is in the form of tablets or capsules.

3. A composition according to claim 2 wherein the zwitterionic compound is a member selected from the group consisting of the $C_{14}$ through $C_{22}$ n-alkyl N,N-dimethylammonio trioxaundecanoate zwitterionic compounds, and ester salts thereof.

4. A tablet or capsule according to claim 3 containing from about 18 mg. to about 2,500 mg. of the zwitterionic compound or ester salt thereof.

5. A composition according to claim 1 which contains, as an additional ingredient, a safe and effective amount of a conventional antacid.

6. A composition according to claim 4 which contains, as an additional ingredient, a safe and effective amount of a conventional antacid.

7. A composition according to claim 5 or claim 6 wherein the antacid is selected from the group consisting of sodium bicarbonate, aluminum hydroxide, magnesium oxide, magnesium carbonate, magnesium-aluminum hydroxide, calcium carbonate, magnesium trisilicate, magnesium hydroxide, and mixtures thereof.

8. A process for managing peptic ulcers in a human or lower animal in need of such treatment by orally administering thereto a safe and effective amount of from about 10 mg/kg to about 3,000 mg/kg per day of a zwitterionic compound of the type of claim 1.

9. A process according to claim 8 wherein the dosage rate is about 25 mg/kg/day–500 mg/kg/day.

10. A process according to claim 9 wherein the zwitterionic compound is a member selected from the group consisting of the $C_{14}$ through $C_{22}$ n-alkyl N,N-dimethylammonio trioxaundecanoate zwitterionic compounds, and ester salts thereof.

11. A process according to claim 8 or 10 wherein the zwitterionic compound or ester thereof is administered in conjunction with a conventional antacid.

* * * * *